(12) United States Patent
Sekido

(10) Patent No.: US 11,258,222 B2
(45) Date of Patent: Feb. 22, 2022

(54) CABLE CONNECTION STRUCTURE, ENDOSCOPE, AND METHOD OF MANUFACTURING CABLE CONNECTION STRUCTURE

(71) Applicant: OLYMPUS CORPORATION, Tokyo (JP)

(72) Inventor: Takanori Sekido, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/224,292

(22) Filed: Apr. 7, 2021

(65) Prior Publication Data
US 2021/0226396 A1 Jul. 22, 2021

Related U.S. Application Data

(63) Continuation of application No. PCT/JP2018/038372, filed on Oct. 15, 2018.

(51) Int. Cl.
| | |
|---|---|
| *H01R 12/50* | (2011.01) |
| *H05K 1/11* | (2006.01) |
| *H01R 43/02* | (2006.01) |
| *A61B 1/00* | (2006.01) |
| *H01R 12/53* | (2011.01) |

(52) U.S. Cl.
CPC ......... *H01R 43/0263* (2013.01); *H05K 1/119* (2013.01); *A61B 1/00114* (2013.01); *A61B 1/00124* (2013.01); *H01R 12/53* (2013.01); *H05K 2201/09063* (2013.01); *H05K 2201/09409* (2013.01); *H05K 2201/10356* (2013.01)

(58) Field of Classification Search
CPC ........ H01R 12/50–592; H01R 43/0256; H01R 43/0263; H05K 1/119
See application file for complete search history.

(56) References Cited

U.S. PATENT DOCUMENTS

| | | |
|---|---|---|
| 2013/0005181 A1 | 1/2013 | Yamada et al. |
| 2018/0132704 A1 | 5/2018 | Yamada et al. |

FOREIGN PATENT DOCUMENTS

| | | |
|---|---|---|
| JP | H07-135037 A | 5/1995 |
| JP | H08-340058 A | 12/1996 |
| JP | 4906964 B2 | 3/2012 |
| WO | 2011/125502 A1 | 10/2011 |
| WO | 2017013745 A1 | 1/2017 |

OTHER PUBLICATIONS

International Search Report dated Dec. 25, 2018 issued in PCT/JP2018/038372.
English Abstract of WO 2010/070853 A1 dated Jun. 24, 2010.

*Primary Examiner* — Jeremy C Norris
(74) *Attorney, Agent, or Firm* — Scully, Scott, Murphy & Presser, P.C.

(57) ABSTRACT

A cable connection structure includes: a substrate that includes: an opening; and a core wire connection electrode that is arranged on one of a principle surface and an inner layer across the opening; a cable that is arranged on a principle surface side of the substrate and includes a core wire that is electrically connected to the core wire connection electrode, the core wire connection electrode being extended so as to be separated from the substrate, the core wire connection electrode being connected to the core wire.

14 Claims, 13 Drawing Sheets

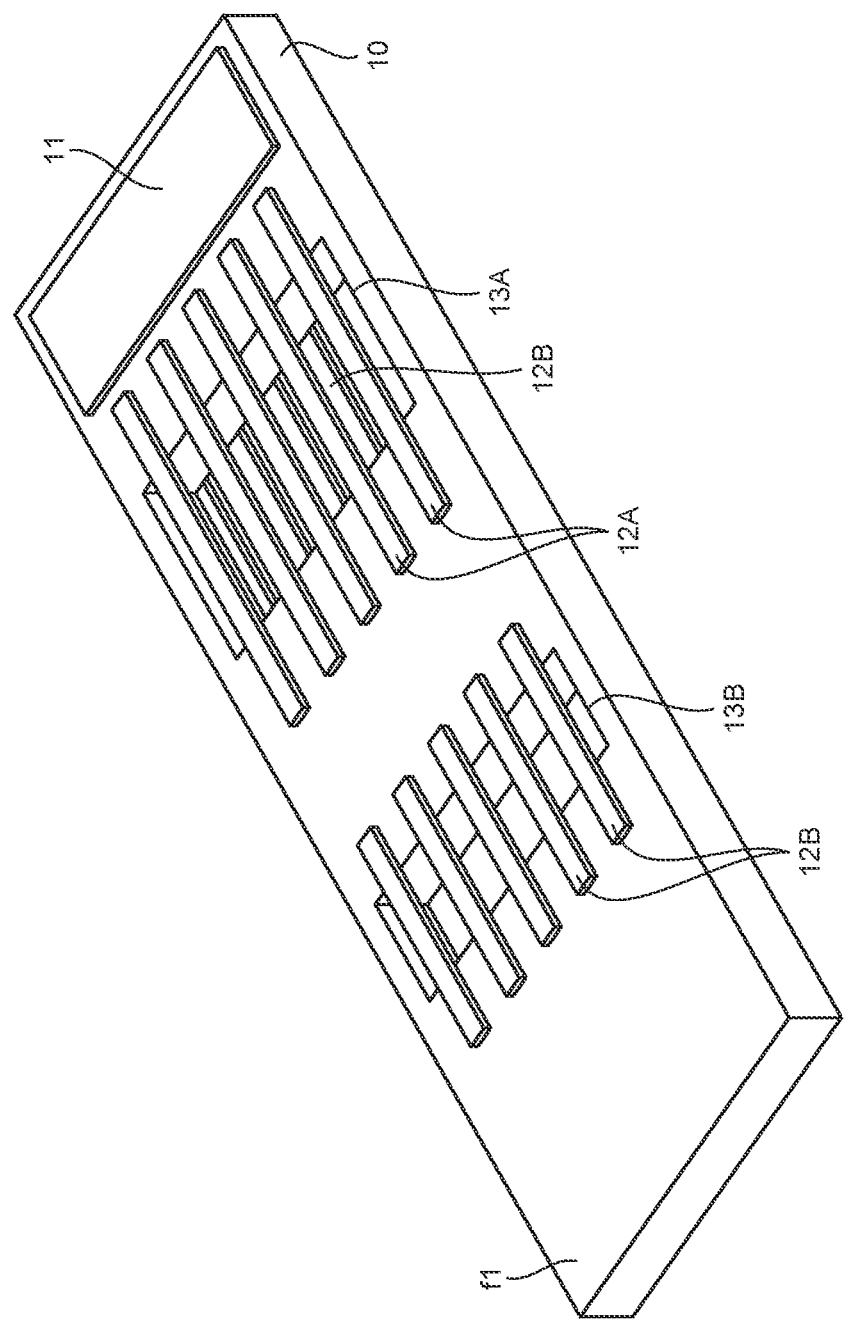

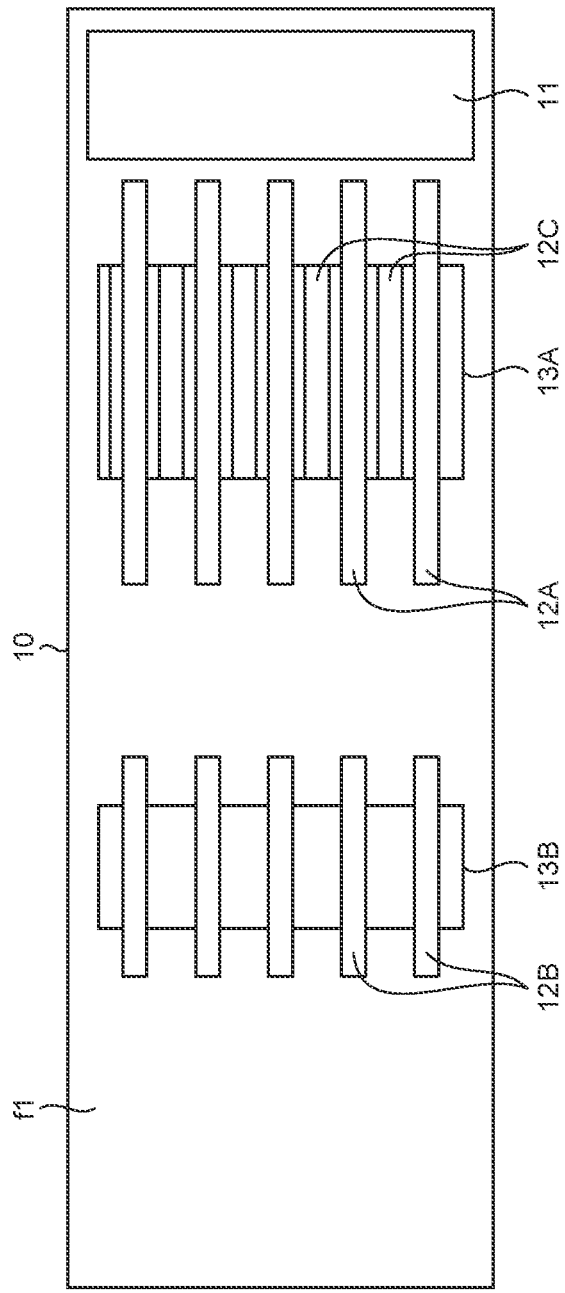

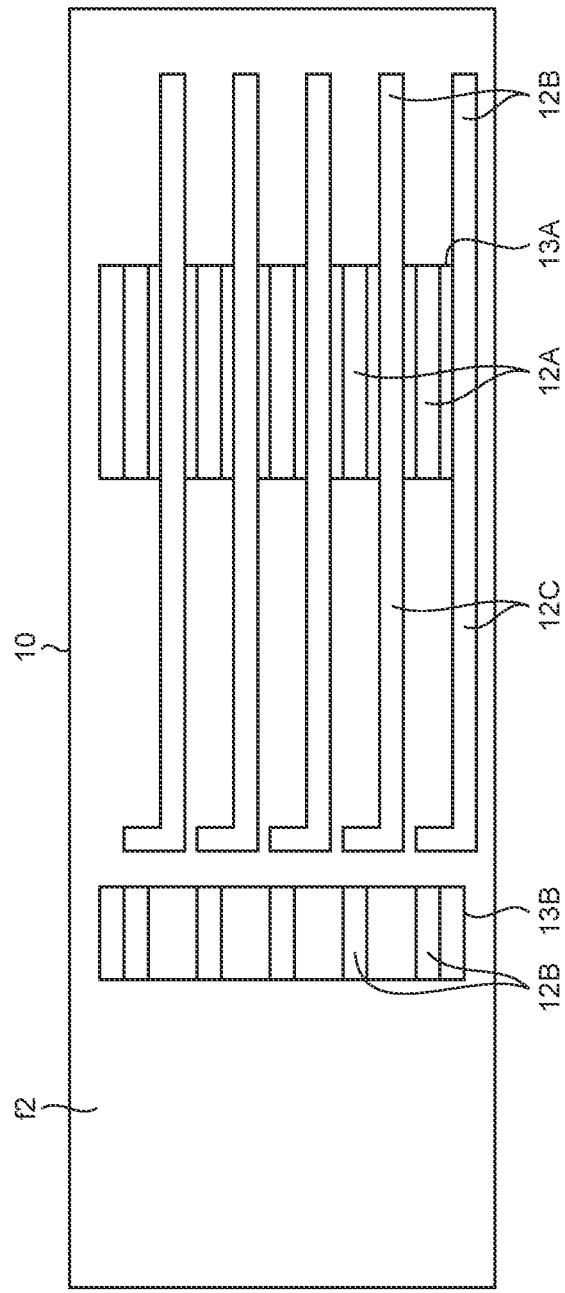

CABLE CONNECTION STRUCTURE, ENDOSCOPE, AND METHOD OF MANUFACTURING CABLE CONNECTION STRUCTURE

CROSS-REFERENCE TO RELATED APPLICATION

This application is a continuation of International Application No. PCT/JP2018/038372, filed on Oct. 15, 2018, the entire contents of which are incorporated herein by reference.

BACKGROUND

1. Technical Field

The present disclosure relates to a cable connection structure, an endoscope, and a method of manufacturing the cable connection structure.

2. Related Art

In the related art, an endoscope, by inserting a flexible insertion portion provided with an imaging device at a distal end thereof into a subject, such as a patient, causes an imaging device arranged on a distal end portion to acquire image data of an inside of the subject and transmits the image data to an external information processing device. A plurality of cables are used to transmit and receive driving power, a clock signal, and the like in addition to the image data, and the plurality of cables are connected to a substrate of the imaging device.

In recent years, with thinning of a core wire of a cable, a technology for forming, on a cable connection electrode on a substrate to which the cable is connected, a groove for fitting the core wire and a shield line has been disclosed (see Japanese Laid-open. Patent Publication. No. H7-135037). According to the technology in Japanese Laid-open Patent Publication No. H7-135037, it is possible to cause a core Wire and a shield line of a coaxial cable to fall in the formed groove, so that it is possible to connect the coaxial cable to the substrate without positional misalignment and it is possible to prevent the core wire from bending at the time of connection.

SUMMARY

In some embodiments, a cable connection structure includes: a substrate that includes: an opening; and a core wire connection electrode that is arranged on one of a principle surface and an inner layer across the opening; a cable that is arranged on a principle surface side of the substrate and includes a core wire that is electrically connected to the core wire connection electrode, the core wire connection electrode being extended so as to be separated from the substrate, the core wire connection electrode being connected to the core wire.

In some embodiments, an endoscope includes the cable connection structure.

In some embodiments, provided is a method of manufacturing a cable connection structure. The method includes: adjusting a position of a cable on a principal surface side of a substrate; inserting a distal end portion of a connection tool into an opening arranged in the substrate from a back surface side of the substrate; applying pressure and heat to a core wire of the cable and a core wire connection electrode that is arranged on one of a principal surface and an inner layer across the opening, with the inserted distal end portion of the connection tool and a backup member that is arranged on a principal surface side of the substrate; extending the core wire connection electrode so as to be separated from the substrate; and connecting the core wire connection electrode to the core wire by a conductive member.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a perspective view of a substrate used in the cable connection structure in FIG. 2;

FIG. 5 is a plan view of the substrate in FIG. 4 when viewed from a principal surface f1 side;

FIG. 6 is a plan view of the substrate 10 in FIG. 4 when viewed from a back surface f2 side;

DETAILED DESCRIPTION

Figure 1:
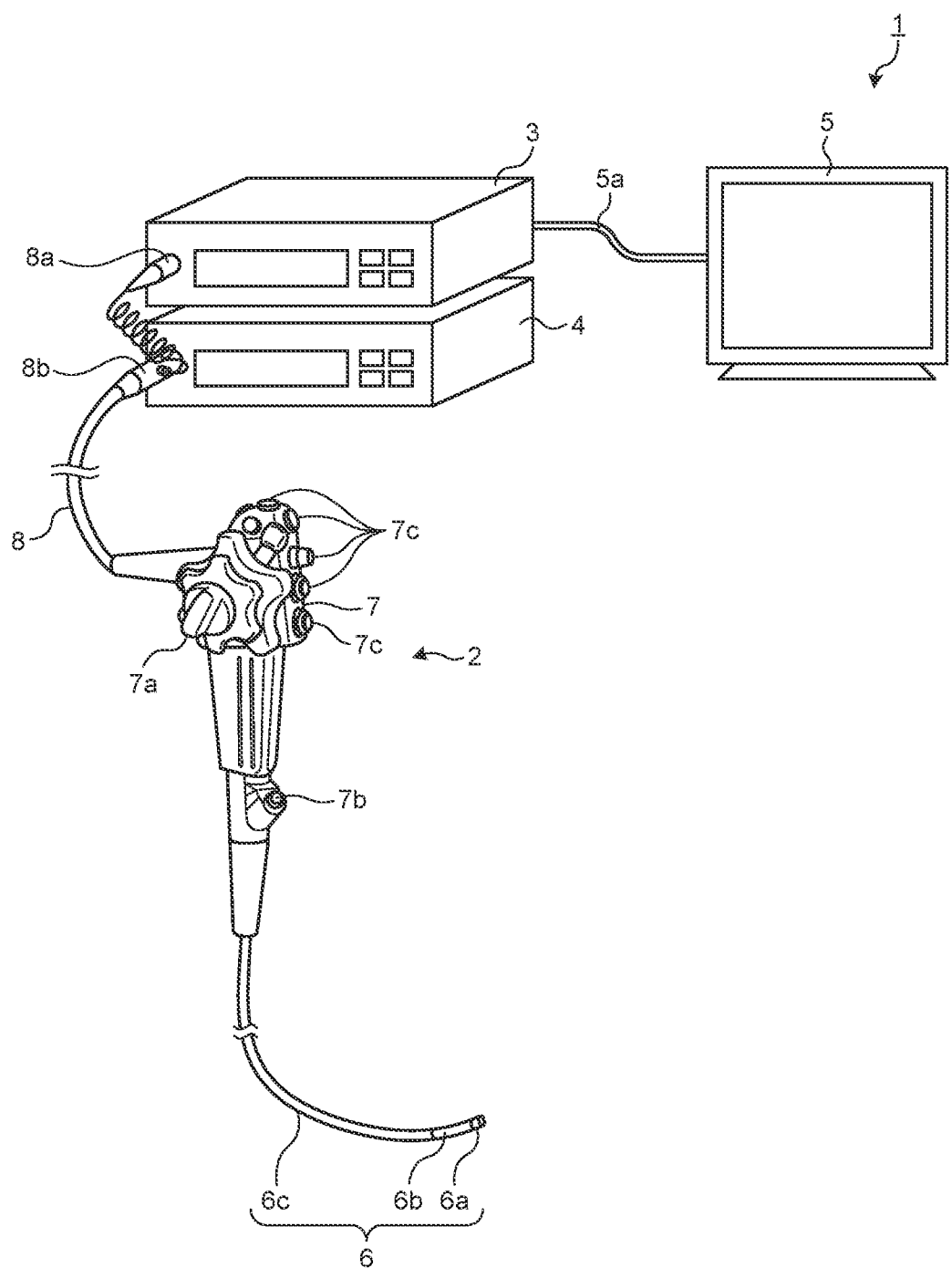
FIG. 1 is a diagram schematically illustrating an entire configuration of an endoscope system according to a first embodiment of the present disclosure.

As modes for carrying out the present disclosure (hereinafter, referred to as "embodiments"), an endoscope system including a cable connection structure will be described below. The present disclosure is not limited by the embodiments below. Furthermore, in the drawings referred to in the description below, shapes, sizes, and positional relationships are only schematically illustrated so that the contents of the present disclosure may be understood. In other words, the present disclosure is not limited to only the shapes, the sizes, and the positional relationships illustrated in the drawings. Moreover, the drawings may include portions that have different dimensional relations or ratios.

First Embodiment

FIG. 1 is a diagram schematically illustrating an entire configuration of an endoscope system 1 according to a first embodiment of the present disclosure. As illustrated in FIG. 1, the endoscope system 1 according to the present embodiment includes an endoscope 2 that is introduced into a subject, that captures an image of an inside of the subject, and that generate an image signal of the inside of the subject, an information processing device 3 that performs predetermined image processing on the image signal captured by the endoscope 2 and that controls each of units of the endoscope system 1, a light source device 4 that generates illumination light of the endoscope 2, and a display device 5 that displays an image of the image signal subjected to the image processing by the information processing device 3.

The endoscope 2 includes an insertion portion 6 that is inserted into the subject, an operating unit 7 that is arranged on a proximal end portion side of the insertion portion 6 and that is gripped by an operator, and a flexible universal cord 8 that is extended from the operating unit 7.

The insertion portion 6 is implemented by using a light guide formed of an illumination fiber, an electrical cable, an optical fiber, or the like. The insertion portion 6 includes a distal end portion 6a that is provided with a built-in imaging device (to be described later), a bending portion 6b that includes a plurality of bending pieces and that is freely bendable, and a flexible tube portion 6c that is arranged on a proximal end portion side of the bending portion 6b and that has flexibility. In the distal end portion 6a, an illumination unit that illuminates the inside of the subject via an illumination lens, an observation unit that captures an image of the inside of the subject, an opening that is communicated with a treatment tool channel, and air/water supply nozzles (not illustrated).

The operating unit 7 includes a bending knob 7a that causes the bending portion 6b to bend in a vertical direction and in a horizontal direction, a treatment tool insertion portion 7b for inserting a treatment tool, such as a biopsy forceps or a laser scalpel, into a body cavity of the subject, and a plurality of switch portions 7c for performing operation on the information processing device 3, the light source device 4, and peripheral devices, such as an air supply device, a water supply device, and a gas supply device. The treatment tool inserted from the treatment tool insertion portion 7b gets out of an opening at a distal end of the insertion portion 6 through the treatment tool channel that is internally arranged.

The universal cord 8 is configured with a light guide formed of an illumination fiber, a cable, or the like. A proximal end of the universal cord 8 is bifurcated, and one end of a branch serves as a connector 8a, and a proximal end of the other branch serves as a connector 8b. The connector 8a is detachably attachable to a connector of the information processing device 3. The connector 8b detachably attachable to the light source device 4. The universal cord 8 propagates illumination light emitted from the light source device 4 to the distal end portion 6a via the connector 8b and the light guide formed of the illumination fiber. Further, the universal cord 8 transmits an image signal captured by the imaging device (to be described later) to the information processing device 3 via the cable and the connector 8a.

The information processing device 3 performs predetermined image processing on the image signal output from the connector 8a and controls the entire endoscope system 1.

The light source device 4 is configured with a light source that emits light, a condenser lens, or the like. The light source device 4 emits light from the light source and supplies the light, as illumination light for the inside of the subject that is an object, to the connected endoscope 2 via the connector 8b and the light guide formed of the illumination fiber in the universal cord 8, under the control of the information processing device 3.

The display device 5 is configured with a display or the like made of liquid crystal or organic electro luminescence (EL). The display device 5 displays, via a video cable 5a, various kinds of information including the image subjected to the predetermined image processing by the information processing device 3. With this configuration, an operator is able to observe a desired position inside the subject and determine symptoms by operating the endoscope 2 while viewing an image (in-vivo image) displayed by the display device 5.

Figure 2:
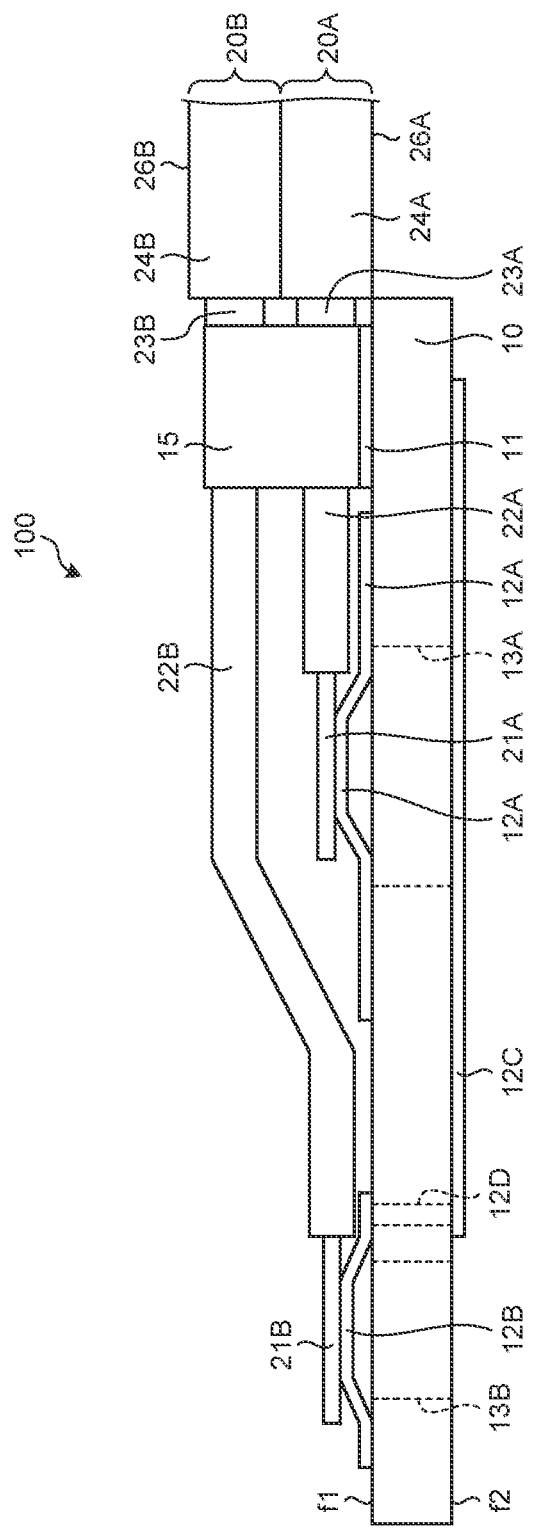
FIG. 2 is a side view of a cable connection structure used in an endoscope according to the first embodiment of the present disclosure.
Figure 3:
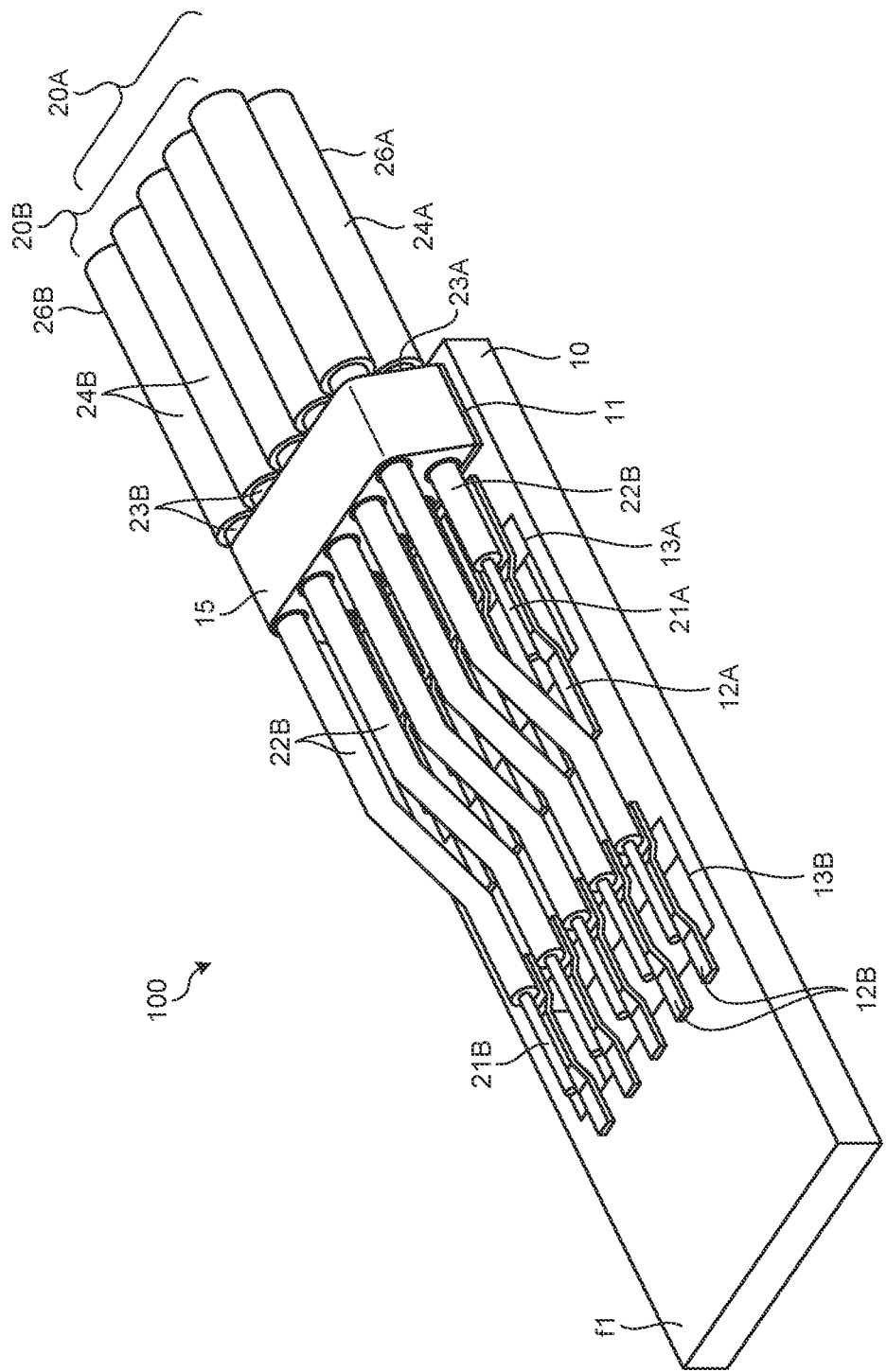
FIG. 3 is a perspective view of the cable connection structure in FIG. 2.

A cable connection structure 100 used in the endoscope system 1 will be described in detail below. FIG. 2 is a side view of the cable connection structure 100 used in the endoscope 2 according to the first embodiment of the present disclosure. FIG. 3 is a perspective view of the cable connection structure 100 in FIG. 2. FIG. 4 is a perspective view of a substrate 10 used in the cable connection structure 100 in FIG. 2 when viewed from a principal surface f1 side. FIG. 5 is a plan view of the substrate 10 in FIG. 4 when viewed from the principal surface f1 side. FIG. 6 is a plan view of the substrate 10 in FIG. 4 when viewed from a back surface f2 side.

The cable connection structure 100 includes the substrate 10, a lower side assembly cable 20A, and an upper side assembly cable 20B.

The substrate 10 includes a shield line connection electrode 11 for connecting shield lines 23A of the lower side assembly cable 20A, first core wire connection electrodes 12A for connecting core wires 21A of the lower side assembly cable 20A, second core wire connection electrodes 12B for connecting core wires 21B of the upper side assembly cable 20B, a rectangular first opening 13A, and a second opening 13B. The first core wire connection electrodes 12B are arranged across the first opening 13A and the second core wire connection electrodes 12B are arranged across the second opening 13B, in other words, each of them is arranged as a bride from one end side to an opposing end side of the corresponding opening over the first opening 13A or the second opening 13B.

The shield Line connection electrode 11 is arranged in a proximal end portion of the principal surface f1 of the substrate 10, and the first core wire connection electrodes 12A are arranged on a center side of the principal surface f1 of the substrate 10 relative to the shield line connection electrode 11. The second core wire connection electrodes 12B are arranged at positions that are more separated from the shield line connection electrode 11 than the first core wire connection electrodes 12A on the principal surface f1 of the substrate 10. Meanwhile, in the present specification, the proximal end portion of the substrate 10 is located in a direction in which the lower side assembly cable 20A and the upper side assembly cable 20B are extended.

The second core wire connection electrodes 12B are wired onto the principal surface f1 from conductor patterns 12C that are arranged on the back surface f2 of the substrate 10 through vias 12D. The conductor patterns 12C arranged on the back surface f2 are arranged so as not co overlap with the first core wire connection electrodes 12A when viewed from the principal surface f1 side. By arranging the conductor patterns 12C on the back surface f2 so as not to overlap with the first core wire connection electrodes 12A when viewed from the principal surface f1 side, it is possible to prevent a connection tool and the conductor patterns 12C from coming into contact with each other and prevent the conductor patterns 12C from being damaged when the connection tool is brought into contact with the core wire connection electrodes 12A from the back surface f2 side. Furthermore, by forming the conductor patterns 12C on the back surface f2, it is possible to increase a distance between a certain one of the core wire connection electrodes 12A and a certain one of the conductor patterns 12C, which is connected to the core wire connection electrode 12A adjacent to the certain core wire connection electrode 12A, by a length equal to a thickness of the substrate 10 as compared to a case in which the conductor patterns 12C are arranged on the principal surface f1, so that it is possible to prevent a short circuit between flying leads (the conductor patterns 12C and the first core wire connection electrodes 12A) even when a pitch distance of the core wire connection electrodes 12A is small.

The lower side assembly cable 20A includes a plurality of coaxial cables 26A. Each of the coaxial cables 26A includes the core wire 21A, a dielectric 22A that covers a periphery of the core wire 21A, the shield line 23A that covers a periphery of the dielectric 22A, and a jacket 24A that covers a periphery of the shield line 23A. In the coaxial cable 26A, the jacket 24A, the shield line 23A, and the dielectric 22A are removed such that the core wire 21A, the dielectric 22A, and the shield line 23A are exposed in a stepwise manner.

The shield lines 23A of the lower side assembly cable 20A are directly connected to the shield line connection electrode 11 by a conductive member 15, such as solder. The core wires 21A of the lower side assembly cable 20A are electrically connected to the first core wire connection electrodes 12A by a conductive member (not illustrated).

The upper side assembly cable 20B includes a plurality of coaxial cables 26B. Each of the coaxial cables 26B includes the core wire 21B, a dielectric 22B that covers a periphery of the core wire 21B, a shield line 23B that covers a periphery of the dielectric 22B, and a jacket 24B that covers a periphery of the shield line 23B. In the coaxial cable 26B, the jacket 24E, the shield line 23E, and the dielectric 22B are removed such that the core wire 21B, the dielectric 22B, and the shield line 23B are exposed in a stepwise manner.

The shield lines 23B of the upper side assembly cable 20B are connected to the shield line connection electrode 11 by the conductive member, such as solder, via the shield lines 23A of the lower side assembly cable 20A. The core wires 21B of the upper side assembly cable 20B are connected to the second core wire connection electrodes 12B by a conductive member (not illustrated).

A method of manufacturing the cable connection structure 100 will be described below with reference to FIG. 7A to FIG. 7E. FIG. 7A to FIG. 7E are diagrams for explaining the method of manufacturing the cable connection structure 100 in FIG. 2.

Figure 7A:
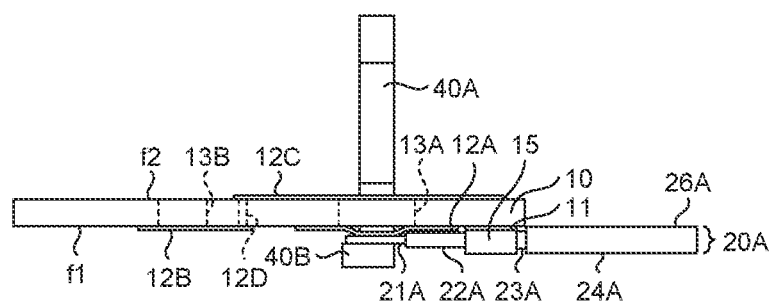
FIG. 7A to FIG. 7E are diagrams for explaining a method of manufacturing the cable connection structure in FIG. 2.
Figure 7B:
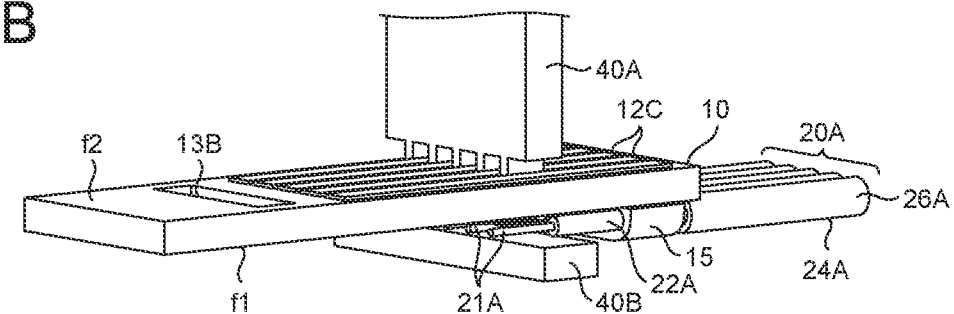
Figure 7C:
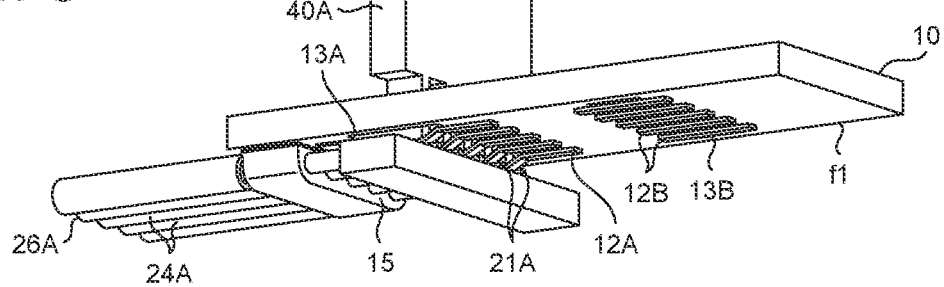

A position of the lower side assembly cable 20A is adjusted to the principal surface f1 side of the substrate 10, the shield lines 23A of the lower side assembly cable 20A are connected to the shield line connection electrode 11 by the conductive member 15, a distal end portion of a connection tool 40A is subsequently inserted into the first opening 13A from the back surface f2 side of the substrate 10 as illustrated in FIG. 7A to FIG. 7C, and the core wires 21A of the coaxial cables 26A and the first core wire connection electrodes 12A that are arranged on the principal surface f1 across the first opening 13A are pressurized and heated with the inserted distal end portion of the connection tool 40A and a backup member 40B that is arranged on the principal surface f1 side of the substrate 10, and are connected by a conductive member (not illustrated). The connection tool 40A has a shape in which a distal end portion is divided so as to come into contact with only the first core wire connection electrodes 12A without coming into contact with the conductor patterns 12C. The backup member 40B is installed at a position at which the core wires 21A do not bend. By inserting the connection tool 40A into the first opening 13A from the back surface f2 side, the first core wire connection electrodes 12A wired on the principal surface f1 (the first opening 13A) of the substrate 10 are extended and connected to certain positions at which the first core wire connection electrodes 12A come into contact the with the core wires 21A. When the connection tool 40A is inserted into the first opening 13A, the positions of the core wires 21A are fixed by the backup member 40B, so that the core wires 21A do not bend in a direction away from the principal surface f1 and in a direction approaching the principal surface f1 due to the connection, and it is possible to reduce the possibility of disconnection. After the core wires 21A and the first core wire connection electrodes 12A are connected, the connection tool 40A and the backup member 40B are moved.

Figure 7D:
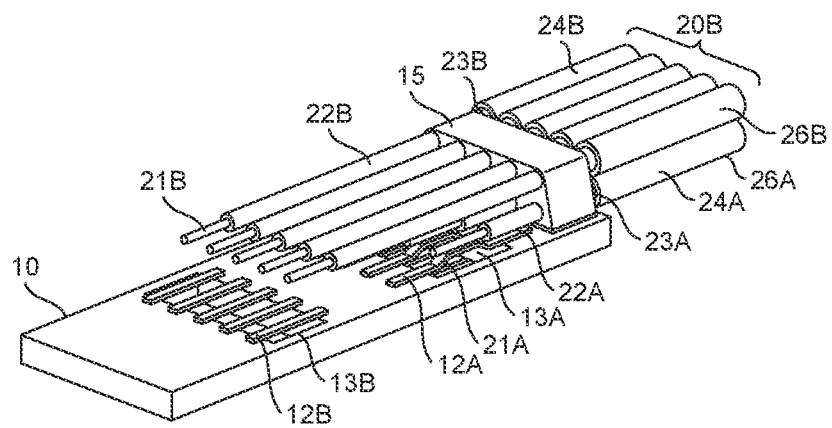

After the core wires 21A of the lower side assembly cable 20A are connected to the first core wire connection electrodes 12A, as illustrated in FIG. 7D, the shield lines 23B of the upper side assembly cable 20B are connected onto the shield lines 23A of the lower side assembly cable 20A by a conductive member, such as solder. With this connection, the shield lines 23B of the upper side assembly cable 20B are connected to the shield line connection electrode 11 via the shield lines 23A.

Figure 7E:
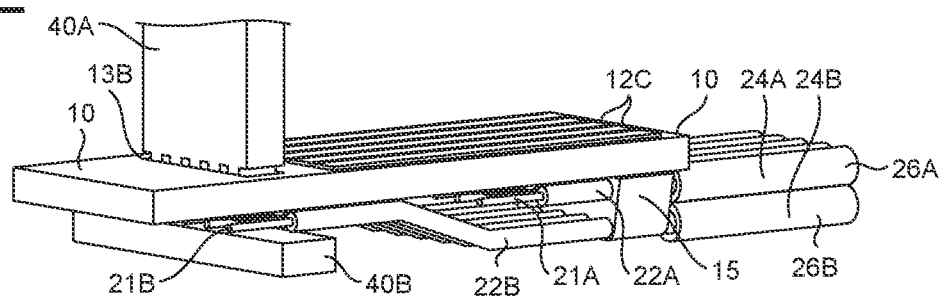

After the shield lines 23B of the upper side assembly cable 20B are connected to the shield lines 23A by the conductive member 15, as illustrated in FIG. 7E, the distal end portion of the connection tool 40A is inserted into the second opening 13B from the back surface f2 side of the substrate 10, and the core wires 21B of the coaxial cables 26B and the second core wire connection electrodes 12B that are arranged on the principal surface f1 across the second opening 13B are pressurized and heated with the inserted distal end portion of the connection tool 40A and the backup member 40B that is arranged on the principal surface f1 side of the substrate 10, and are connected by a conductive member (not illustrated). When the connection tool 40A is inserted into the second opening 13B, the positions of the core wires 21B are fixed by the backup member 40B, so that the core wires 21B do not bend due to the connection, and it is possible to reduce the possibility of disconnection.

As described above, in the first embodiment, the first core wire connection electrodes 12A and the second core wire connection electrodes 12B are extended and connected to the core wires 21A and the core wires 21B, so that it is possible to prevent the core wires 21A and the core wires 21B from bending and prevent the possibility or disconnection. Furthermore, in the first embodiment, the first core wire connection electrodes 12A are arranged across the first opening 13A, so that even after the upper side assembly cable 20B is connected to the substrate 10, it is possible to repair connection portions between the first core wire connection electrodes 12A and the core wires 21A through the first opening 13A. Moreover, in the first embodiment, the coaxial cables 26A and 26B are connected to the substrate 10 in a vertically two-stage manner, so that it is possible to reduce a mounting area, and when used in the endoscope 2 or the like, it is possible to reduce a size of the endoscope 2 or the like.

First Modification of First Embodiment

Figure 8:
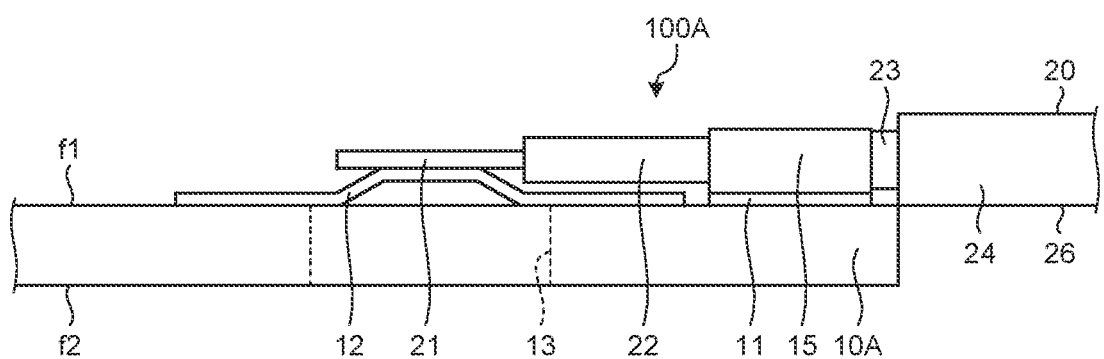
FIG. 8 is a side view of a cable connection structure according to a first modification of the first embodiment of the present disclosure.

In the first embodiment, the assembly cables 20A and 20B are connected to the substrate 10 in a vertically two-stage manner; however, an assembly cable 20 may be connected to the substrate 10 in a single stage manner. FIG. 8 is a side view of a cable connection structure 100A according to a first modification of the first embodiment of the present disclosure.

The cable connection structure 100A includes a substrate 10A and the assembly cable 20.

The substrate 10A includes the shield line connection electrode 11 for connecting shield lines 23 of the assembly cable 20, core wire connection electrodes 12 for connecting core wires 21 of the assembly cable 20, and a rectangular opening 13. The core wire connection electrodes 12 are arranged across the opening 13, in other word, arranged as bridges from one end side to an opposing end side of the opening over the opening 13.

The assembly cable 20 includes a plurality of coaxial cables 26, each including the core wire 21, a dielectric 22 that covers a periphery of the core wire 21, the shield line 23 that covers a periphery of the dielectric 22, and a jacket 24 that covers a periphery of the shield line 23. In the coaxial cable 26, the jacket 24, the shield line 23, and the dielectric 22 are removed such that the core wire 21, the dielectric 22, and the shield line 23 are exposed in a stepwise manner.

The shield lines 23 of the assembly cable 20 are connected to the shield line connection electrode 11 by a conductive member, such as solder, and the core wires 21 are connected to the core wire connection electrodes 12 by a conductive member (not illustrated).

In the first modification of the first embodiment, similarly to the first embodiment, the core wire connection electrodes 12 are extended and connected to the core wires 21, so that it is possible to prevent the core wires 21 from bending and it is possible to prevent the possibility of disconnection.

In the first modification of the first embodiment, the core wires 21 of the assembly cable 20 including the plurality of coaxial cables 26 are connected to the core wire connection electrodes 12 of the substrate 10A, but even if the single coaxial cable 26 is connected to the core wire connection electrode 12 that is arranged across the opening 13, it is possible to prevent the core wire 21 from bending and it is possible to prevent the possibility of disconnection. Furthermore, as for a core wire of a single-wire cable instead of the coaxial cable 26, by similarly connecting the core wire to a core wire connection electrode that is arranged across an opening formed on a substrate, it is possible to achieve the same effects as described above. Moreover, in the first embodiment and the first modification, the core wire connection electrodes are arranged on the principal surface of the substrate, but embodiments are not limited to this example, and it is possible to achieve the same effects even if the core wire connection electrodes are arranged, across an opening, on an inner layer of a multi-layer substrate.

Second Modification of First Embodiment

Figure 9:
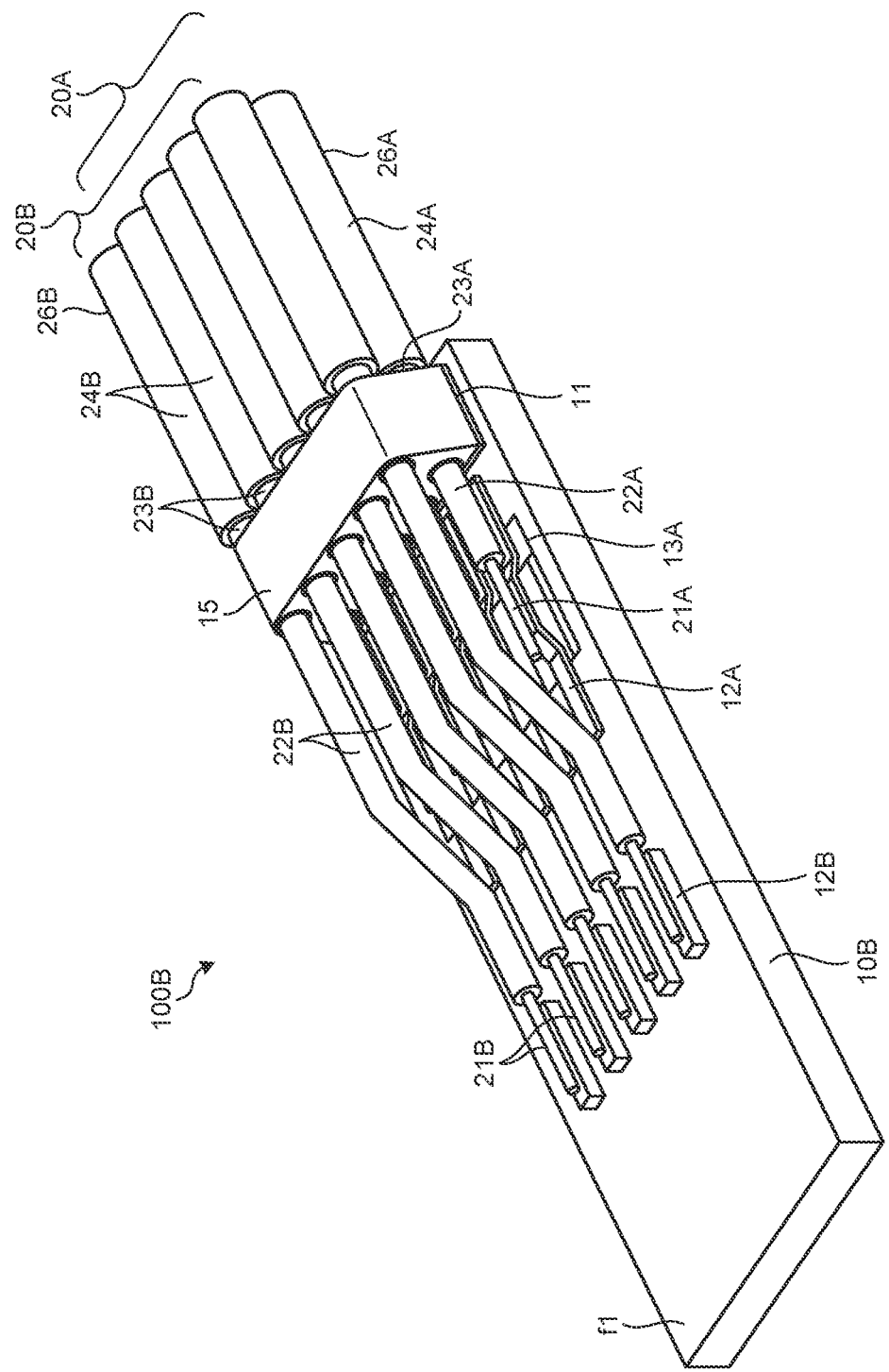
FIG. 9 is a perspective view of a cable connection structure according to a second modification of the first embodiment of the present disclosure.

In the first embodiment the substrate 10 includes the first opening 13A and the second opening 13B; however, in a second modification, the substrate 10 includes only the first opening 13A. FIG. 9 is a perspective view of a cable connection structure 100B according to the second modification of the first embodiment of the present disclosure.

The cable connection structure 100B includes a substrate 10B, the lower side assembly cable 20A, and the upper side assembly cable 20B.

The substrate 10B includes the shield line connection electrode 11 for connecting the shield lines 23A of the lower side assembly cable 20A, the first core wire connection electrodes 12A for connecting the core wires 21A of the lower side assembly cable 20A, the second core wire connection electrodes 12B for connecting the core wires 21B of the upper side assembly cable 20B, and the rectangular first opening 13A. The first core wire connection electrodes 12A are arranged across the first opening 13A. The second core wire connection electrodes 12B are arranged on the principal surface f1 of the substrate 10B.

The core wires 21A of the lower side assembly cable 20A are connected, by a conductive member (not illustrated), to the first core wire connection electrodes 12A that extend on the core wires 21A side. At the time of the connection, the core wire 21A does not bend, so that the possibility of disconnection is reduced.

The second core wire connection electrodes 12B have larger thicknesses than those of the first core wire connection electrodes 12A. For example, the thicknesses of the second core wire connection electrode 12B are set so as to be approximately equal to thicknesses of the dielectrics 22B. Therefore, when the core wires 21B of the upper side assembly cable 20B are connected to the second core wire connection electrodes 12B, it is possible to prevent the core wires 21B from bending, so that it is possible to reduce the possibility of disconnection of the core wires 21B.

Second Embodiment

Figure 10A:
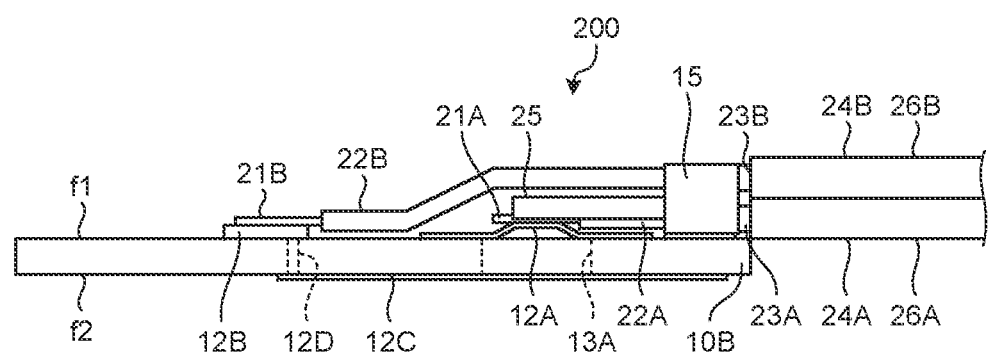
FIG. 10A is a side view and FIG. 10B is a perspective view of a cable connection structure according to a second embodiment of the present disclosure.
Figure 10B:
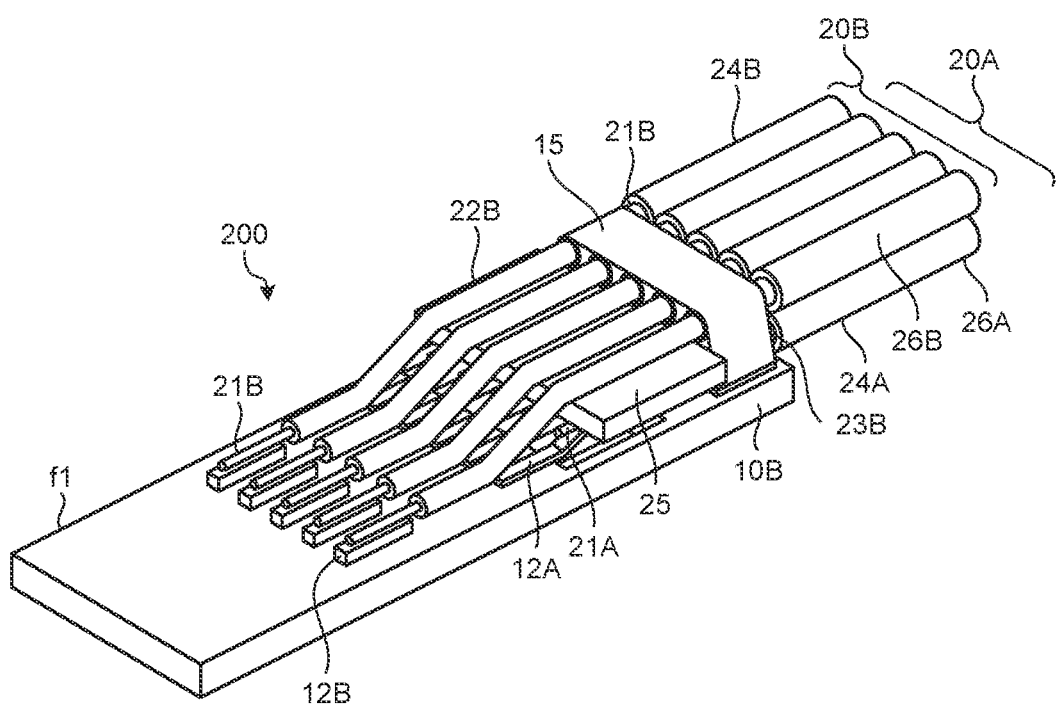

A cable connection structure 200 according to a second embodiment includes a backup member. FIG. 10A is a side view and FIG. 10B is a perspective view of the cable connection structure according to the second embodiment of the present disclosure.

In the cable connection structure 200, an insulating backup member 25 is fixed around the exposed dielectrics 22A and the exposed core wires 21A of the lower side assembly cable 20A on a side that does not come into contact with the substrate 10B. The backup member 25 has a function to fix the core wires 21A in a non-bending manner when the core wires 21A and the first core wire connection electrodes 12A are connected to one another.

A method of manufacturing the cable connection structure 200 will be described below with reference to the drawings. FIG. 11A to FIG. 11G are diagrams for explaining the method of manufacturing the cable connection structure 200 in FIG. 10A and FIG. 10B.

Figure 11A:
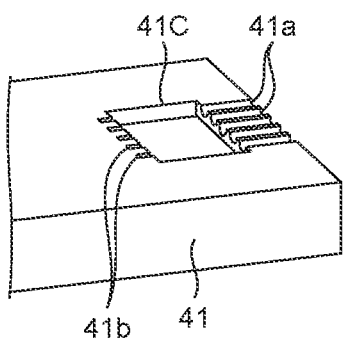
FIG. 11A to FIG. 11G are diagrams for explaining a method of manufacturing the cable connection structure in FIG. 10A and FIG. 10B.

First, a mold 41 as illustrated in FIG. 11A is prepared. The mold 41 includes grooves 41a for arranging the exposed shield lines 23A of the coaxial cables 26A, grooves 41b for arranging distal end portions of the exposed core wires 21A, and a frame 41C for forming the backup member 25 around proximal end portions of the exposed core wires 21A and the exposed dielectrics 22A.

Figure 11B:
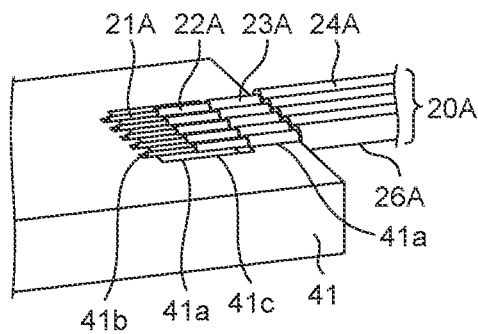

As illustrated in FIG. 11B, the coaxial cables 26A included in the lower side assembly cable 20A are arranged in the mold 41, and thereafter, the frame 41C is filled with resin, the resin is cured, and the backup member 25 is fixed around the dielectrics 22A and the core wires 21A. It is preferable to form the backup member 25 such that about a half of the periphery of each of the core wires 21A is exposed because the core wires 21 are connected to the first core wire connection electrodes 12A.

Figure 11C:
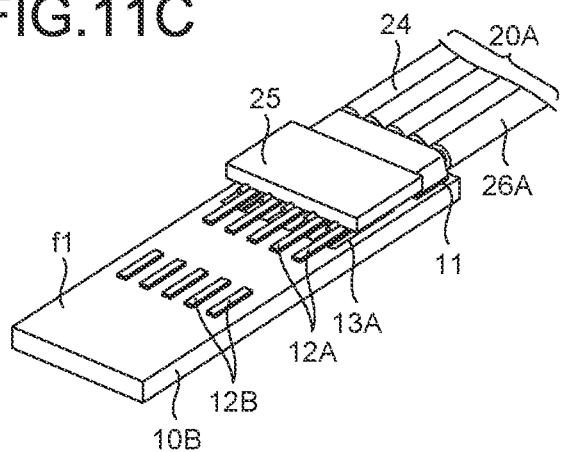
Figure 11E:
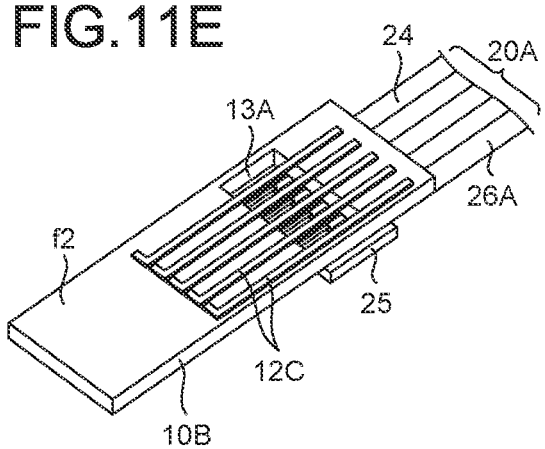
Figure 11D:
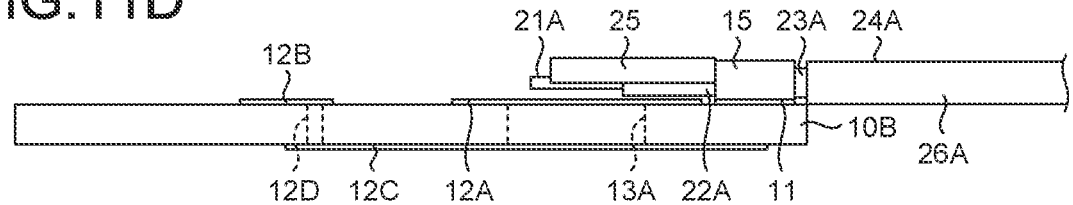

A position of the lower side assembly cable 20A for which the backup member 25 is fixed around the core wires 21A and the dielectrics 22A is adjusted to the principal surface f1 side of the substrate 10B, and, as illustrated in FIG. 11C and FIG. 11D, the shield lines 23A of the lower side assembly cable 20A are connected to the shield line connection electrode 11 by the conductive member 15.

Figure 11F:
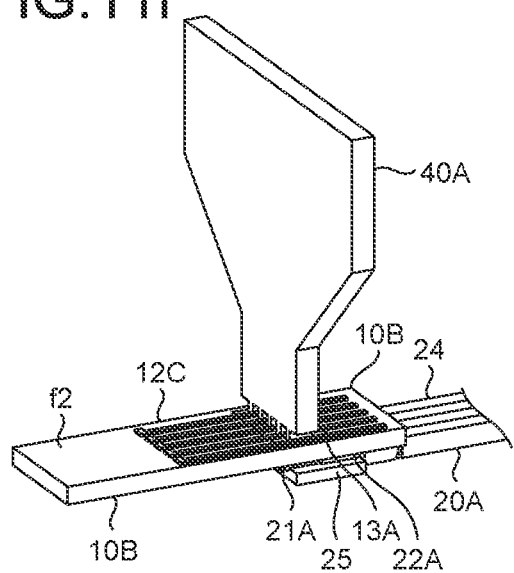
Figure 11G:
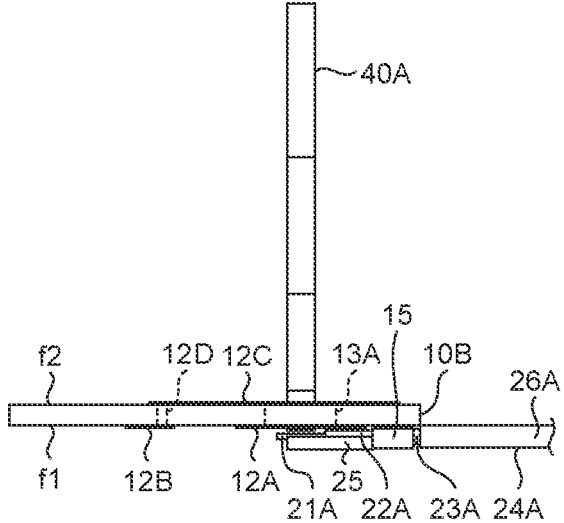

After the shield lines 23A are connected, as illustrated in FIG. 11E to FIG. 11G, the distal end portion of the connection tool 40A is inserted into the first opening 13A from the back surface f2 side of the substrate 10B, and the core wires 21A of the coaxial cables 26A and the first core wire connection electrodes 12A that are arranged on the principal surface f1 across the first opening 13A are pressurized and heated with the inserted distal end portion of the connection tool 40A and the backup member 25 that is fixed around the dielectrics 22A and the core wires 21A, and are connected by a conductive member (not illustrated) The connection tool 40A has a shape in which the distal end portion is divided so as to come into contact with only the first core wire connection electrodes 12A without coming into contact with the conductor patterns 12C. The backup member 25 fixes the core wires 21A, so that by inserting the connection tool 40A into the first opening 13A from the back surface f2 side, it is possible to extend and connect the first core wire connection electrodes 12A that are wired on the principal surface f1 (the first opening 13A) of the substrate 10B to certain positions at which the first core wire connection electrodes 12A come into contact with the core wires 21A When the connection tool 40A is inserted into the first opening 13A, the positions of the core wires 21A are fixed by the backup member 25, so that the core wires 21A do not bend due to the connection and it is possible to reduce the possibility of disconnection.

After the core wires 21A are connected to the first core wire connection electrodes 12A, the shield lines 23B of the upper side assembly cable 20B are connected to the shield lines 23A, and the core wires 21B are connected to the second core wire connection electrodes 12B.

The cable connection structure 200 according to the second embodiment needs a process of fixing the backup member 25; however, it is possible to fix the arrangement of the core wires 21A by the backup member 25, so that it is possible to improve reliability of connection.

Third Embodiment

Figure 12A:
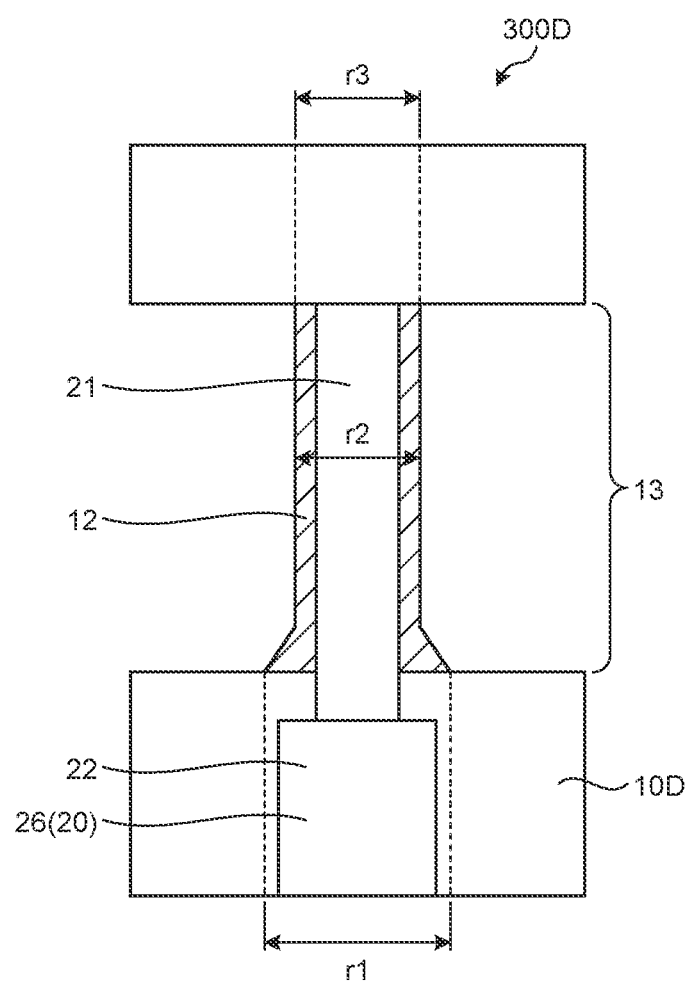
FIG. 12A is a partially enlarged plan view of a cable connection structure according to a third embodiment of the present disclosure.

In a cable connection structure according to a third embodiment, a width of each of the core wire connection electrodes 12 above the opening 13 is smaller than a width on a proximal end side of the opening 13. FIG. 12A is a partially enlarged plan view of a cable connection structure 300D according to the third embodiment of the present disclosure.

The cable connection structure 300D includes a substrate 10D and the assembly cable 20.

The substrate 10D includes the shield line connection electrode 11 (not illustrated) for connecting the shield lines 23 of the assembly cable 20, the core wire connection electrodes 12 for connecting the core wires 21 of the assembly cable 20, and the rectangular opening 13. The core wire connection electrodes 12 are arranged across the opening 13, in other words, arranged as bridges from one end side to an opposing end side of the opening over the opening 13.

The assembly cable 20 includes the plurality of coaxial cables 26, each including the core wire 21, the dielectric 22 that covers the periphery of the core wire 21, the shield line 23 (not illustrated) that covers the periphery of the dielectric 22, and the jacket 24 (not illustrated) that covers the periphery of the shield line 23. In the coaxial cable 26, the jacket 24, the shield line 23, and the dielectric 22 are removed such that the core wire 21, the dielectric 22, and the shield line 23 are exposed in a stepwise manner. FIG. 12A illustrates the vicinity of the opening 13 of the single coaxial cable 26 included in the assembly cable 20.

In the core wire connection electrode 12, a width r2 above the opening 13 is smaller than a width r1 on the proximal end side of the opening 13. By setting, in the core wire connection electrode 12, the width r2 above the opening 13 to be smaller than the width r1 on the proximal end side of the opening 13, it is possible to prevent a short circuit. Further, by maintaining, in the core wire connection electrode 12, the longer width r1 on the proximal end side of the opening 13 than the width r2 above the opening 13, when a load in a peeling direction (direction in which the substrate 10D and the assembly cable 20 are peeled off each other) is applied to the assembly cable 20, because the width r1 of the core wire connection electrode 12 on the proximal end side of the opening 13, which serves as a base point of breaking of a connection portion (connection end portion of the core wire 21), is long, it is possible to prevent breaking of the connection portion.

In the third embodiment, the case has been described in which the assembly cable 20 is connected to the substrate 10D in the single stage manner; however, even in the first core wire connection electrodes 12A and the second core wire connection electrodes 12B of the cable connection structure 100 of the first embodiment, by setting widths of the first core wire connection electrodes 12A and the second core wire connection electrodes 12B above the first opening 13A and the second opening 13B to be smaller than widths on the proximal end sides of the first opening 13A and the second opening 13B, it is possible to achieve the same effects.

Figure 12B:
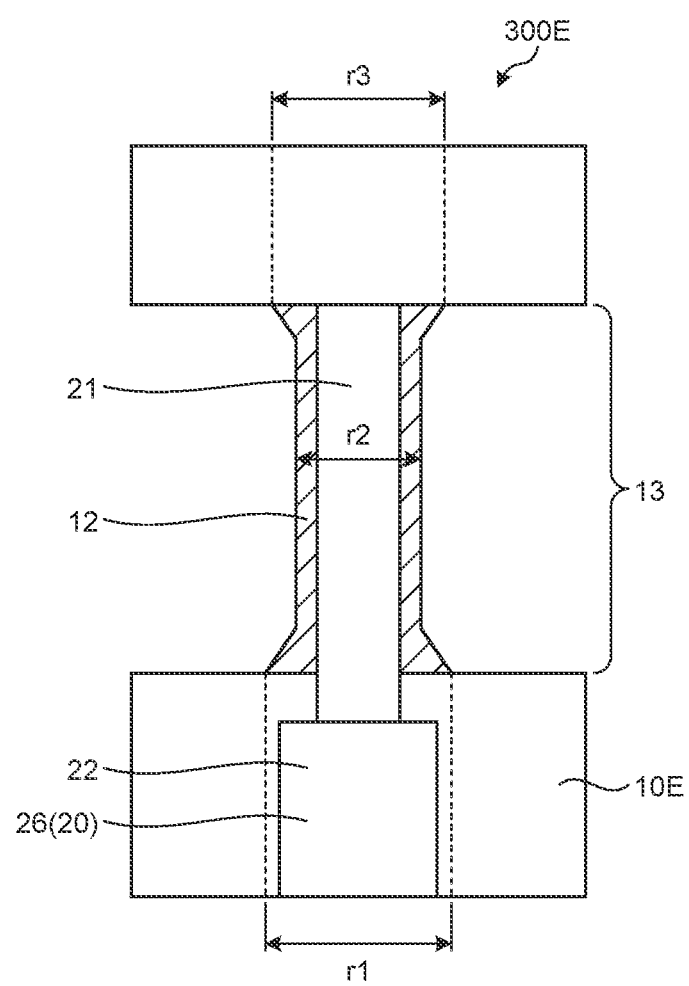
FIG. 12B is a partially enlarged plan view of a cable connection structure according to a modification of the third embodiment of the present disclosure.

Furthermore, in the third embodiment, a width r3 of the core wire connection electrode 12 on a distal end side is set to be equal to the width r2 above the opening 13, but it may be possible to set the width r3 of the core wire connection electrode 12 on a distal end side of the opening 13 to be larger than the width r2 above the opening 13. FIG. 12B is a partially enlarged plan view of a cable connection structure 300E according to a modification of the third embodiment of the present disclosure. FIG. 12B illustrates the vicinity of the opening 13 of the single coaxial cable 26 included in the assembly cable 20.

In the cable connection structure 300E, the width r2 of the core wire connection electrode 12 above the opening 13 is set to be smaller than the width r1 on the proximal end side of the opening 13 and the width r3 on the distal end side of the opening 13. By setting the width r2 of the core wire connection electrode 12 above the opening 13 to be smaller than the width r1 on the proximal end and the width r3 on the distal end side of the opening 13, it is possible to prevent a short circuit. Furthermore, by maintaining, in the core wire connection electrode 12, the longer width r1 on the proximal end side of the opening 13 and the longer width r3 on the distal end side of the opening 13 than the width r2 above the opening 13, when a load in a peeling direction (direction in which a substrate 10E and the assembly cable 20 are peeled off each other) is applied to the assembly cable 20, because the widths r1 and r3 of the core wire connection electrode 12 on the proximal end side and the distal end side of the opening 13 serving as base points of breaking of a connection portion (connection end portion of the core wire 21) is long, it is possible to prevent breaking of the connection portion.

According to the present disclosure, it is possible to connect a core wire and a core wire connection electrode without bending the core wire, so that it is possible to reduce possibilities of disconnection and a short circuit.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection structure comprising:
    a substrate that includes:
        an opening; and
        a core wire connection electrode that is arranged on one of a principle surface and an inner layer across the opening;
    a cable that is arranged on a principle surface side of the substrate and includes a core wire that is electrically connected to the core wire connection electrode, the core wire connection electrode being extended so as to be separated from the substrate, the core wire connection electrode being connected to the core wire.

2. The cable connection structure according to claim 1, wherein
    the core wire connection electrode is one of a plurality of core wire connection electrodes,
    the cable is one of a plurality of cables,
    the plurality of core wire connection electrodes are arranged across the opening, and
    each of core wires of the plurality of cables is connected to each of the plurality of core wire connection electrodes.

3. The cable connection structure according to claim 1, wherein
    the substrate includes a shield line connection electrode on a proximal end side of the principal surface,
    the cable is a coaxial cable that includes the core wire, a dielectric configured to cover a periphery of the core wire, a shield line configured to cover a periphery of the dielectric, and a jacket configured to cover a periphery of the shield line, the cable being formed such that the core wire, the dielectric, and the shield line are exposed in a stepwise manner, and
    the exposed core wire and the exposed shield line are connected to the core wire connect iron electrode and the shield line connection electrode, respectively.

4. The cable connection structure according to claim 3, wherein
    the cable includes:
        a lower side assembly cable in which a shield line is directly connected to the shield line connection electrode; and
        an upper side assembly cable in which a shield line is connected to the shield line connection electrode via the shield line of the lower side assembly cable, and
    a second core wire connection electrode to which a core wire of the upper side assembly cable is connected is arranged at a position that is separated from the shield line connection electrode relative to a first core wire connection electrode to which a core wire of the lower side assembly cable is connected.

5. The cable connection structure according to claim 4, wherein
    the first core wire connection electrode is arranged across the opening,
    the second core wire connection electrode is arranged on the principal surface side by electrical connection through a via from a conductor pattern that is arranged on a back surface,
    the conductor pattern that is arranged on the back surface and that is connected to the second core wire connection electrode is arranged in a region that does not overlap with the first core wire connection electrode when viewed from the principal surface side, and
    the first core wire connection electrode is extended so as to be separated from the substrate and is connected to the core wire.

6. The cable connection structure according to claim 4, wherein
    the substrate includes a first opening and a second opening,
    the first core wire connection electrode is arranged across the first opening,
    the second core wire connection electrode is arranged across the second opening, and
    the first core wire connection electrode and the second core wire connection electrode are extended so as to be separated from the substrate and are connected to the core wire of the lower side assembly cable and the core wire of the upper side assembly cable, respectively.

7. The cable connection structure according to claim 4, wherein
    the substrate includes a first opening,
    the first core wire connection electrode is arranged across the first opening,
    the second core wire connection electrode is arranged on the principal surface and has a thickness equal to a thickness of the dielectric, and
    the first core wire connection electrode is extended so as to be separated from the substrate and is connected to the lower side assembly cable.

8. The cable connection structure according to claim 4, wherein an insulating backup member is fixed around the exposed dielectric and the exposed core wire of the lower side assembly cable on a side that is not in contact with the substrate.

9. The cable connection structure according to claim 1, wherein the core wire connection electrode is formed such that a width above the opening is smaller than at least a width on a proximal end side of the opening.

10. An endoscope including the cable connection structure according to claim 1.

11. A method of manufacturing a cable connection structure, the method comprising:
    adjusting a position of a cable on a principal surface side of a substrate;
    inserting a distal end portion of a connection tool into an opening arranged in the substrate from a back surface side of the substrate;
    applying pressure and heat to a core wire of the cable and a core wire connection electrode that is arranged on one of a principal surface and an inner layer across the opening, with the inserted distal end portion of the connection tool and a backup member that is arranged on a principal surface side of the substrate;
    extending the core wire connection electrode so as to be separated from the substrate; and
    connecting the core wire connection electrode to the core wire by a conductive member.

12. The method of manufacturing the cable connection structure according to claim 11, wherein the cable is a coaxial cable that includes the core wire, a dielectric configured to cover a periphery of the core wire, a shield line configured to cover a periphery of the dielectric, and a racket configured to cover a periphery of the shield line, the cable being formed such that the core wire, the dielectric, and the shield line are exposed in a stepwise manner, the method further comprising connecting the exposed shield line to a shield line connection electrode by a conductive member, the shield line connection electrode being formed on a proximal end side of the principal surface of the substrate, and applying pressure and heat to the core wire of the cable and the core wire connection electrode with the connection tool and the backup member, and connecting the core wire of the cable and the core wire connection electrode by the conductive member.

13. The method of manufacturing the cable connection structure according to claim 12, wherein the cable includes a lower side assembly cable and an upper side assembly cable, the method further comprising connecting a shield line of the lower side assembly cable to a shield line connection electrode by the conductive member, the shield line connection electrode being formed on a proximal end side of the principal surface of the substrate, inserting the distal end portion of the connection tool into the opening from the back surface side of the substrate, applying pressure and heat to a core wire of the lower side assembly cable and a first core wire connection electrode that is arranged on one of the principal surface and an inner layer across the opening, with the inserted distal end portion of the connection tool and the backup member that is arranged on the principal surface side of the substrate, extending the core wire connection electrode so as to be separated from the substrate, connecting the core wire connection electrode to the core wire of the lower side assembly cable by the conductive member, connecting a shield line of the upper side assembly cable onto a shield line of the lower side assembly cable by the conductive member, and connecting a core wire of the upper side assembly cable to a second core wire connection electrode by the conductive member, the second core wire connection electrode being arranged on the principal surface of the substrate.

14. The method of manufacturing the cable connection structure according to claim 13, further comprising:

fixing an insulating backup member around the exposed dielectric and the exposed core wire of the lower side assembly cable on a side that is not in contact with the substrate;

applying pressure and heat to the core wire of the lower side assembly cable and the first core wire connection electrode with the distal end portion of the connection tool that is inserted into the opening from the back surface side of the substrate, and the backup member that is fixed around the dielectric and the core wire; and connecting the core wire of the lower side assembly cable and the first core wire connection electrode by the conductive member.

\* \* \* \* \*